United States Patent [19]

Savaides et al.

[11] Patent Number: 5,350,572
[45] Date of Patent: * Sep. 27, 1994

[54] PERMANENT WAVING COMPOSITION

[75] Inventors: Andrew Savaides, Norwalk; Ludwig Salce, Greenwich, both of Conn.

[73] Assignee: Shiseido Co., Ltd., Tokyo, Japan

[*] Notice: The portion of the term of this patent subsequent to Sep. 7, 2000 has been disclaimed.

[21] Appl. No.: 19,207

[22] Filed: Feb. 18, 1993

[51] Int. Cl.$^5$ .................... A61K 7/09; A61K 7/06
[52] U.S. Cl. .......................... 424/71; 424/72; 132/202; 132/205
[58] Field of Search ............... 424/71, 72; 514/706, 514/712

[56] References Cited

U.S. PATENT DOCUMENTS

| 2,719,814 | 10/1955 | Haefele | 429/72 |
| 2,719,815 | 10/1955 | Sanders | 424/72 |
| 3,472,820 | 10/1969 | Kalopissis | 424/72 |
| 3,768,490 | 10/1973 | Kalopissis | 424/72 |
| 3,840,656 | 10/1974 | Kalopissis | 424/72 |
| 4,333,987 | 6/1982 | Kwart | 428/419 |
| 4,750,482 | 6/1988 | Sieverding | 128/156 |
| 5,162,389 | 11/1992 | Lee | 522/42 |

OTHER PUBLICATIONS

CA (98): 209367t (1983).
CA (107): 83682a (1987).
CA (108): 7704q (1988).

Primary Examiner—Thurman K. Page
Assistant Examiner—Sally Gardner
Attorney, Agent, or Firm—Melvin I. Stoltz

[57] ABSTRACT

An entirely new class of reducing agents with substantially enhanced beneficial results is attained by employing polyoxyethyleneglycol dimercaptoalkylester compounds in a permanent waving lotion. This new class of reducing agents are water soluble, non-volatile and provide a substantially reduced malodor effect. Furthermore, by employing the dithiol compounds of the present invention as the reducing agent, long lasting hair conditioning and enhanced physical attributes, such as shine, luster, softness, manageability, and hair thickness, are also realized.

12 Claims, No Drawings

PERMANENT WAVING COMPOSITION

TECHNICAL FIELD

This invention relates to the art of permanently waving hair, and more particularly, to a new class of compounds which can be employed as reducing agents to provide substantially increased, long-lasting, durable permanently waved hair while also substantially reducing the malodor typically associated with permanent waving.

BACKGROUND ART

The permanent waving of hair is a well established and well developed art in which substantial attention has been directed to improve the present level of technology. Although substantial changes have occurred throughout the last decades, various problems continue to plague the industry in spite of numerous attempts to reduce or eliminate these problems.

In order to best understand the present state of the art and the problems existing therein, it is important to reiterate that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S-S) to give keratin protein (K-S-S-K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free—SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

(i) 

(ii) 

(iii) 

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

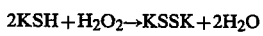

The most commonly used reducing agents employed in the permanent deformation of hair keratin are salts and esters of thioglycolic acid. Other less commonly reducing agents include cysteine, cysteamino, thiolactic acid and their derivatives. These reducing agents are very effective in the reduction of disulfide bonds and under certain conditions can reduce more than 50% of the keratin cystine bonds.

Although effective in providing excellent reducing capabilities, the above mercaptans and their corresponding derivatives possess problems that are difficult to control. One of the disadvantages is the emission of mal odor, which is very common with sulfur compounds. This characteristic creates discomfort to both the stylist and the individual who undergoes permanent waving. Therefore, fragrances are used with reducing agents to mask unpleasant sulfur odors. Other disadvantages include the irreversible fiber alteration as made evident by increased fiber porosity and decreased tensile properties.

Much efforts have been expended in attempts to minimize these attributes. These include pretreatments, barriers which decrease the rate of diffusion, reduction of the mercaptan concentration and/or the pH of the reducing agents, and duration of reduction time. Many of these pretreatments yield other undesirable characteristics such as oily, greasy, and dirty feeling the hair fiber.

Furthermore, in the art of permanent waving, there is much trial and error, with the hair being over-processed, in some instances. The characteristics of over-processing are raspy feel to the hair or a loss of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical changes in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Therefore, it is a principal object of the present invention to provide a composition for permanently waving hair fibers which is capable of imparting to the head of hair a durable, long-lasting permanent hair set retention, while substantially eliminating the mal odor typically resulting from the waving process.

Another object of the present invention is to provide a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition having the characteristic features described above which is capable of imparting a long-lasting permanent wave or setting property to the hair, while substantially reducing hair damage caused during the reduction and oxidation processes.

A further object of the present invention is to provide a permanent wave composition having the characteristic features described above which is capable of improving the elastic and tensile properties of the hair fibers.

Other and more specific objects will in part be obvious and will in part appear hereinafter.

DETAILED DESCRIPTION

By employing the present invention, the prior art limitations and difficulties have been overcome and a long-lasting, permanently waved head of hair is attained, which substantially reduces mal odor typically associated therewith. In addition, the permanent waving lotion of the present invention imparts long lasting hair conditioning and enhanced physical properties to the hair fibers, such as shine, luster, softness, manageability and hair thickness.

In accordance with the present invention, the desirable and previously unattainable enhanced characteristics are realized by employing a reducing agent which comprises an entirely new class of compounds. It has been found that these previously unattainable goals are realized by employing a new class of dithiol compounds. These compounds are water soluble, non-volatile, and have reduced sulfide odor.

The new class of dithiol, water soluble compounds of this invention comprise polyoxyethyleneglycol dimercaptoalkylester (POEDMAE) which are defined by Formula I detailed below:

FORMULA I $R—OCH_2CH_2(—OCH_2CH_2)_nOCH_2CH_2O—R'$ where n is 2 to 33, and

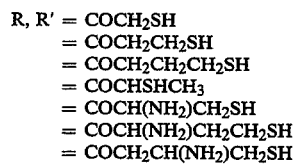

Preferably, the new class of dithiol compounds defined by Formula I are prepared by reacting polyoxyethyleneglycol (Compound A) with the corresponding organic mercaptan (Compound B) having a carboxylic acid functionality. This reaction is illustrated by the following:

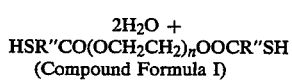

where n is 2 to 33, and

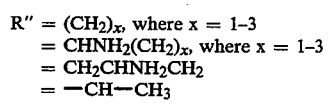

The organic mercaptans, represented by Compound B, are exemplified by thioglycolic acid, thiolactic acid, thioproprionic acid, and cysteine. The esterification reaction of polyoxyethyleneglycol (Compound A) with the organic mercaptan (Compound B) is preferably carried out under vacuum at a temperature ranging between about 95° C. and 110° C. In addition, the reaction is conducted in the presence of an acid as the catalyst. Trifluoracetic acid is one example of an acid usable in this regard, since it has been found to be efficacious as the catalyst for this reaction.

In the preferred process, the acid catalyst is employed after the stoichiometric amount of Compound A and Compound B have been intermixed. It has also been found, if desired, that this reaction may be pushed further to the right by using a small excess of Compound A.

The present invention differs from our co-pending U.S. patent application relating to formulations and application methods for permanent wave enhancements in that the dithiol compounds defined by Formula I have been found to be employable as hair keratin reducing agents. In our previous disclosure, the mono or dimercapto polyoxyethylene compounds detailed therein are employable as additives to a generally conventional reducing lotion or, if desired, as a separate application for the hair fibers after the removal of the reducing lotion. In the present invention, the dithiol compounds defined by Formula I are employed as the sole source of the hair keratin reducing agent.

For purposes of complete disclosure, and not in any way intending to limited thereby, the following reactions are presented as demonstrating the mechanism by which hair keratin (cystine) reduction occurs by employing the new, dithiol compounds defined by Formula I:

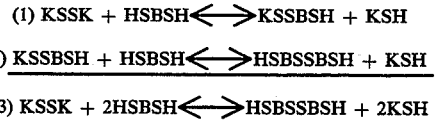

Mechanism of Hair Keratin Reduction (1) KSSK + HSBSH ⇌ KSSBSH + KSH (2) KSSBSH + HSBSH ⇌ HSBSSBSH + KSH (3) KSSK + 2HSBSH ⇌ HSBSSBSH + 2KSH wherein KSSK=keratin disulfides; KSH=reduced keratin; HSBSH=compounds of general Formula I and KSSBSH=mixed disulfide In the preferred embodiment of this invention, the dithiol compound defined by Formula I is employed in a reducing lotion in which the dithiol reducing agent comprises between about 5% and 40% by weight. Although this range has been found to provide acceptable permanent waving results, it preferred that the polyoxyethylene glycol dimercaptoalkylesters defined in Formula I ranges between about 20% and 30% by weight of the overall reducing lotion.

In addition, the pH of the reducing lotion should be between about 6.5 and 10, with a pH ranging between about 8 and 9.5 being preferred. In order to attain the desired pH level, an alkaline agent selected from the group consisting of ammonia, monoethanolamine, diethanolamine, triethanolamine, ammonium carbonate, and bicarbonate are preferably employed.

In the preferred embodiment, the reducing lotion also incorporates other additives for imparting additional benefits to the resulting permanently waved hair. These additives include protein hydrolyzates, conditioning agents, fragrances, ionic or non-ionic wetting agents, chelating agents, such as EDTA and penetrating agents, such as urea, pyrrolidone and phytantriol.

In employing the permanent waving lotion of the present invention, it has been found that the reducing agent is preferably applied to moisten hair that has been previously rolled on rollers and allow to remain on the moistened hair for between about 10 and 60 minutes. Although this range has been found to be effective, the lotion is preferably allowed to remain on the hair for between about 5 and 30 minutes. If desired, the reaction may be accelerate by applying heat to the hair. Although any conventional temperature may be employed, a temperature of about 50° C. has been found to be most effective.

Once the desired reaction time has been achieved, the hair is rinsed with water and blotted to remove excess moisture. Then, the hair is neutralized or oxidized with a solution which incorporates one or more agents selected from the group consisting of acidic hydrogen peroxide, alkaline bromate or sodium chlorite. Preferably, these oxidizing solutions are applied to the hair and allowed to remain for between about 2 and 10 minutes. However, alternate time ranges can be employed, without departing from the scope of the invention. In addition, it has been found that most desirable results are attained when the concentration of the oxidizing solution is varied depending upon which oxidizing agent is employed. When acidic hydrogen peroxide is used as the oxidizing solution, its concentration preferably ranges between about 1% and 4% by weight. When alkaline bromate is employed at the oxidizing solution, its preferably ranges from between about 2% and 12% by weight.

In the permanent waving of bleached or porous hair, it has been found that the application of the reducing lotion of the present invention is preferably carried out with the temperature being maintained at about 37° C. However, when the present invention is employed on hair fibers wherein the cuticle is well defined, the use of external heating from a hair dryer has been found to be effective in increasing the rate of reduction. Preferably, the temperature range for such applications ranges between about 40° C. and 75° C.

In preparing the permanent waving lotion in accordance with the present invention, an aqueous solution containing any desired alkaline agents., penetrating agents, chelating agents, wetting agents, fragrances, and conditioning agents is separately prepared. Then, immediately prior to application to the hair, POEDMAE defined by Formula I is intermixed therewith, resulting in a permanent waving reducing lotion ready for immediate use on the desired head of hair. In Table I, an overall formulation for the permanent wave reducing lotion made in accordance with this invention is provided.

TABLE I

| Permanent Wave Reducing Lotion Composition | |
|---|---|
| Ingredient | % by Weight |
| POEDMAE as defined in Formula I | 5%–40% |
| Ionic or Nonionic Detergent | 2%–6% |
| Fragrance | 0.25%–0.40% |
| Ammonium Chloride | 1%–3% |
| Urea | 2%–6% |
| Ethylenediaminetetraacetic Acid | 0.05%–0.50% |
| Ammonia | adjust pH as desired |
| Deionized Water | q.s. to 100% |

By employing the present invention, a substantially improved and enhanced permanently waved head of hair is attained. In addition, the present invention also provides physical characteristics, such as gloss, combability, and softness, while also substantially increasing curl retention or hair set permanency. Furthermore, and of particular importance, is the substantial elimination of malodor which is typically associated with permanently waved hair. As a result, the present invention is capable of eliminating most of the prior art problems, while providing a highly effective reducing lotion for permanently waving heads of hair which is employable in comfort, without causing exposure to unwanted odors and smells.

The invention accordingly comprises the several steps and the relation of one or more of such steps with respect to each of the others, and the composition possessing the features, properties, and relation of components, all as exemplified herein, with the scope of the invention being indicated in the claims.

BEST MODE FOR CARRYING OUT THE INVENTION

In order to substantiate the efficacy of the new class of dithiol reducing agents defined by Formula I of the present invention, the following examples are presented. In this disclosure, the universal applicability of the present invention is fully detailed, along with the ability to permanently wave hair with substantially improved, long-lasting, physical enhancements and characteristics being attained thereby. However, it is to be understood that these examples are intended as a teaching of the best mode for carrying out the present invention and are not intended to limit, in any manner, the breadth of this discovery.

In order to prove the efficacy of the present invention, numerous hair tresses were tested by being permanently waved using the POEDMAE compounds defined by Formula I. In order to provide a standard by which the waving efficiency of the reducing agent defined by Formula I can be objectively evaluated, the "Test Tube Test Curl Method" or excess lotion method was employed.

In the Test Tube Test Curl Method (TTTC), twelve hair fibers are knotted at the root end and cut to a length of 3.5 inches from the knot. The bundle is immersed in water and then wound around an aluminum mandrel having a diameter of 6.5 min. The mandrel is placed in a test tube containing 5 ml of the reducing solution.

Then, the test tube is capped with Parafilm and immersed into a water bath maintained at a constant temperature, usually 37° C. for the prescribed processing time. Once completed, the cold wave solution is drained off, and the test tube and its contents are rinsed three times with water.

After the water has been drained off, 10 ml of the neutralizer is added into the test tube for three minutes. Then, the neutralizer is drained from the mandrel and the coil is immersed in water. Thereafter, both the length and diameter of the resulting curl is recorded.

An acceptable curl has a curl diameter (D) ranging between about 7.0 and 7.5 mm, and a coil length (L) ranging between about 27 and 33 mm. The "deficiency in tightness" or D.I.T. is calculated as follows:

$$D.I.T = \frac{\text{diameter of hair coil (mm)} - \text{diameter of mandrel (mm)}}{\text{diameter of mandrel (mm)}} \times 100$$

As defined in Haefele, U.S. Pat. No. 2,719,814, the D.I.T. is a measurement of the waving efficiency of the reducing solution. Acceptable curls must have a D.I.T. ranging between about 7.5 and 15.4. Although D.I.T. values greater than 100 are possible, they are not of interest.

EXAMPLE 1

In order to demonstrate both the efficacy and the preferred operating parameters for the dithiol reducing agents defined by Formula I of the present invention, numerous tests were conducted wherein the operating parameters of the dithiol concentration, composition pH, and processing time were separately and independently varied. In each of these tests, the dithiol compound defined by Formula I comprised an average molecular weight of 548, with R, R′=COCH$_2$SH and with "n" equalling about 8. Furthermore, the overall reducing lotion composition was consistent with the formulation detailed in Table I.

In the first series of tests, numerous hair samples consisting of European bleached hair obtained from Parrino Hair Goods, Inc. of Commack, N.Y. were employed in order to determine the optimum concentration for the dithiol compounds defined by Formula I. In conducting these tests, the hair fibers were processed for 50 minutes with the solution having a pH of 9.0 and an application temperature of 37° C. The pH level was maintained by employing ammonia.

Following the removal of the reducing lotion, a conventional neutralizer was employed for 3 minutes. In Table II, the test results obtained are provided with the diameter of the resulting curl and the length of the curl being given for the varying concentrations of the dithiol compound. In addition, the deficiency in tightness (D.I.T.) is also provided for each concentration.

TABLE II

| Effect of Concentration of Dithiol Compound On Commercially Bleached Hair Fibers | | | |
|---|---|---|---|
| Dithiol Compound of Formula I % (W/W) | D (mm) | L (mm) | D.I.T. |
| 2.00 | 13.70 | 45.23 | 111.0 |
| 5.00 | 8.48 | 37.36 | 30.5 |
| 20.00 | 7.20 | 34.71 | 10.8 |
| 30.00 | 6.82 | 36.32 | 4.9 |
| 40.00 | 6.89 | 36.40 | 5.2 |

As shown in Table II, the concentration of the dithiol compounds defined by Formula I can be varied from between about 5% to 40% by weight of the permanent waving lotion in order to obtain reasonably effective permanently waved hair. However, as also demonstrated in Table II, the optimum results are attained when the dithiol compound comprises a concentration of about 20%.

Table III provides the results attained by altering the pH of the waving lotion employing the dithiol compounds defined by Formula I. In conducting these tests, the permanent waving lotion and process detailed above in reference to Table II was employed, with the concentration of the dithiol compound being maintained at 20%. In conducting these tests, the pH was varied between 7.00 and 9.00 using ammonia as the alkali.

TABLE III

| Wave Effect Obtained with Variation of pH | | | |
|---|---|---|---|
| pH | D (mm) | L (mm) | D.I.T. |
| 7.00 | 10.10 | 43.20 | 55.4 |
| 8.00 | 7.96 | 38.73 | 22.5 |
| 8.50 | 7.15 | 32.67 | 10.0 |
| 9.00 | 7.21 | 35.19 | 10.9 |

As is apparent from a review of Table III, the dithiol compounds defined by Formula I can be effectively employed in a waving lotion having a pH ranging between about 7.00 and 9.00. However, a pH between about 8 and 9 produced the optimum permanent wave effect.

Table IV provides the results obtained from the tests conducted to determine the optimum processing time. In these tests, the permanent waving lotion and process detailed above in reference to Tables II and III were employed.

In conducting these tests, processing times ranging between 5 minutes and 30 minutes were employed on both commercially prepared bleached hair fibers, as well as laboratory prepared bleached hair fibers. The commercially available bleached hair fibers employed in conducting these tests were identical to the hair fibers detailed above in reference to Table II. The laboratory bleached hair was prepared by treating virgin brown hair with a 20% volume peroxide solution for about 20 minutes at 37° C. Following this exposure, the hair fibers were rinsed with water and shampooed.

TABLE IV

Effects of Processing Time on Permanent Wave Setting For Commercial and Laboratory Bleached Hair Fibers

| Time (min.) | Laboratory Bleached | | | Commercially Bleached | | |
|---|---|---|---|---|---|---|
| | D (mm) | L (mm) | D.I.T. | D (mm) | L (mm) | D.I.T. |
| 5 | 8.65 | 46.3 | 33.0 | 9.48 | 42.50 | 45.8 |
| 10 | 7.98 | 38.40 | 22.8 | 8.14 | 38.16 | 25.2 |
| 20 | 7.02 | 33.40 | 8.0 | 7.35 | 33.32 | 13.1 |
| 30 | 7.35 | 40.93 | 13.1 | 7.22 | 37.23 | 11.08 |

As is evident from a review of Table IV, both laboratory bleached hair fibers and commercially available bleached hair fibers are capable of being permanently waved with processing times ranging between 5 minutes and 30 minutes. However, optimum results are obtained on these bleached hair fibers with processing times ranging between 20 minutes and 30 minutes.

EXAMPLE 2

Unless otherwise specified, the tests in the following examples were conducted using a permanent wave lotion incorporating polyoxyethyleneglycol dimercaptoacetate as the dithiol compound of Formula I. This dithiol compound comprised a molecular weight of 548 and formed a 20% concentration of the permanent waving lotion. In addition, the permanent waving lotion in each instance comprised a pH of 9 and was applied at a temperature of 37° F.

In on order to confirm the reducing efficiency or permanent wave setting of hair fibers attainable with the dithiol compounds defined by Formula I of the present invention, an amino acid analysis was conducted using the excess lotion or immersion method on hair fibers permanently waved with reducing lotions of the present invention using different concentrations of the dithiol compound. In conducting these series of tests, commercially bleached hair, as defined above in reference to Table II was employed.

These hair fibers were first shampooed and then immersed in one of a plurality of different permanent waved lotions having different concentrations of the dithiol compound. After 20 minutes of exposure, the hair fibers were encapped with iodoacetic acid/sodium iodoacetate mixtures. The treated hair fibers were then hydrolyzed with 6N HCl for 24 hours, employing the method disclosed by S. Moore and W. H. Stein in *Methods Enzymol,;* 6 (1963) Page 819.

The amino acid analysis resulting from the hair hydrolyzates for each of the different concentrations of the dithiol compounds are detailed in Table V.

TABLE V

Amino Acid Analysis of Hair Fiber Hydrolyzates

| AMINO ACID ($\mu$moles/Gram Hair) | Concentration of Dithiol Compound (Formula I) | | | | |
|---|---|---|---|---|---|
| | 0% | 5% | 10% | 20% | 30% |
| Cysteine | 346 | 371 | 331 | 366 | 358 |
| CMCysteine | 3 | 74 | 169 | 232 | 318 |
| H.Cyctine | 749 | 657 | 603 | 460 | 307 |

As is evident from a review of the results of Table V, the dithiol compounds of the present invention are capable of providing the desired keratin cystine fiber reduction. The amount of reduction of cystine is dependent upon the concentration of the dithiol compound of Formula I, with concentrations ranging between about 20% and 30% resulting in 38.6% and 59.0% reduction in cystine, respectively. In addition, even at concentration levels of about 5%, a 12.3% cystine reduction was observed.

The amino acid analysis detailed in Table V shows the insignificant formation of mixed disulfides under these experimental conditions. Consequently, this data indicates that the reduction reaction proceeds in accordance with the reaction formulas detailed above.

EXAMPLE 3

In order to unequivocally demonstrate the ability of the dithiol compound of the present invention to substantially reduce the malodor typically associated with permanent waving lotions, odor evaluations of reducing solutions employing the present invention were evaluated by the "olfactory" methodology, as well as by quantitative measurement of the headspace for the presence of hydrogen sulfide. The quantitative analysis of hydrogen sulfide in the headspace was determined by pipetting 50 ml of the waving or reducing solution into a 125 ml erlenmeyer flask, which was subsequently sealed with Parafilm.

After allowing equilibrium stabilization for 3 minutes at 37° C., headspace sampling was performed utilizing a hydrogen sulfide ($H_2S$) sensor tube manufactured by Matheson Gas Products. The amount of hydrogen sulfide measured was then recorded.

For purposes of comparison, the hydrogen sulfide content was also determined in the identical manner for other waving lotions containing ammonium thioglycolate (AMTG) and glycerylmonothioglycolate (GMTG). The comparative assay for hydrogen sulfide headspace content obtained from these tests are detailed in Table VI.

TABLE VI

Comparative Hydrogen Sulfide Headspace Analysis Evaluation of Hydrogen Sulfide Release in Waving Lotions

| Time (min.) | (PPM Hydrogen Sulfide) | | | |
|---|---|---|---|---|
| | 3.00 | 6.00 | 9.00 | 12.00 |
| Headspace Sample Volume (cc) | 100 cc | 200 cc | 300 cc | 400 cc |
| Reducing Agent | | | | |
| 9.20% AMTG, pH 9.20 | 50.0 | 98.0 | 145 | 190.0 |
| 27% GMTG, pH 8.0 | 35 | 63.0 | 90.0 | 118.0 |
| 20% Polyoxyethyleneglycol dimercapto acetate, pH 9.0 | 7 | 27.0 | 46.0 | 68.0 |

As detailed in Table VI, the dithiol compound defined by Formula I of the present invention releases substantially less amounts of hydrogen sulfide than the other, more common reducing agents. Furthermore, the dithiol compounds defined by Formula I were found to exhibit a very low odor during processing and reduction of hair keratin, while also subsequently yielding virtually no post perm odor.

EXAMPLE 4

In order to demonstrate the perming efficiency of the dithiol compounds on most resistant hair, or on hair that has a more defined cuticle, various tests were conducted using the TTTC or excess lotion method. In these experiments, different dithiol compounds defined by Formula I were employed. In each instance, R, $R'=COCH_2SH$ an "n" ranged between 2 and 16. All other conditions were maintained identical to the conditions detailed above. The hair employed was tinted hair and different concentrations of the dithiol compound were tested. The results are provided in Table VII.

TABLE VII

Perming Efficiency on Resistant Hair

| Dithiol Concentration (% by Weight) | M.W 348 | | | M.W 548 | | | M.W. 748 | | |
|---|---|---|---|---|---|---|---|---|---|
| | D (mm) | L (mm) | D.I.T. | D (mm) | L (mm) | D.I.T. | D (mm) | L (mm) | D.I.T. |
| 5.00 | 12.53 | 34.98 | 92.8 | 16.30 | 33.18 | — | 18.58 | 42.83 | — |
| 10.00 | 9.43 | 28.78 | 45.1 | 13.98 | 30.82 | — | 16.90 | 36.63 | — |
| 20.00 | 6.98 | 26.33 | 7.4 | 9.66 | 29.20 | 48.6 | 14.60 | 32.73 | — |
| 30.00 | 7.23 | 28.50 | 11.2 | 9.03 | 27.30 | 38.9 | 12.98 | 30.50 | — |

As is evident from a review of Table VII, a good wave set was realized on hair having a defined cuticle wherein "n" of the dithiol compound ranges between about 3 and 8. Further studies on normal resistant hair at increased temperatures, about 50° C., also produced good wave setting characteristics.. Amino acid analysis of tinted hair fibers processed for thirty minutes at 50° C. showed 34% cystine reduction.

It has also been found that the permanent waving lotion of the present invention can be further enhanced by incorporating therein small amounts of a "reducing booster". Typically, such a reducing booster is preferably selected from the group consisting of ammonium thioglycolate, ammonium thiolactate. glycerylmonothioglycolate, glycerylthiolactate, cysteamine, and cysteine. Preferably, these boosters are employed with dithiol compounds of Formula I where "n" ranges between 2 and 33. Under these conditions, excellent wave sets on hair having defined cuticles have been attained.

In Tables VIII and IX, the results from incorporating small amounts of ammonium thioglycolate (AMTG) and ammonium thiolactate (AMTL) are provided. In both tables, varying amounts of the booster were employed with the dithiol compounds forming a concentration of 30% by weight of the waving lotion. In addition, for purposes of comparison, a permanent waving lotion without any dithiol compound was also tested.

Similarly in Tables X and XI, the results attained from employing glycerylmonothioglycolate (GMTG) and cysteamine as boosters along with the dithiol compound of Formula I are provided. Furthermore, in all of these tests, tinted hair was employed.

TABLE VIII

Perm Efficiency Comparison With Varying Concentrations of Ammonium Thioglycolate

| | Dithiol Compound 30% by Wgt. | | | Dithiol Compound 0% | | |
|---|---|---|---|---|---|---|
| % AMTG | D (mm) | L (mm) | D.I.T. | D (mm) | L (mm) | D.I.T. |
| 1 | 7.83 | 27.85 | 20.5 | 10.16 | 31.3 | 56.3 |
| 2 | 6.92 | 22.04 | 6.5 | 7.90 | 27.32 | 21.5 |
| 4 | 7.05 | 25.98 | 8.5 | 7.07 | 26.13 | 8.8 |
| 6 | 7.33 | 28.5 | 12.8 | 7.13 | 31.43 | 9.7 |

TABLE IX

Perm Efficiency Comparison With Varying Concentrations of Ammonium Thiolactate

| | Dithiol Compound 30% by Wgt. | | | Dithiol Compound 0% | | |
|---|---|---|---|---|---|---|
| % AMTL | D (mm) | L (mm) | D.I.T. | D (mm) | L (mm) | D.I.T. |
| 0 | 9.03 | 27.3 | 38.9 | — | — | |
| 1 | 8.01 | 26.5 | 23.2 | — | — | |
| 2 | 6.98 | 25.83 | 7.4 | 9.18 | 31.50 | 41.2 |
| 4 | 7.20 | 27.89 | 10.8 | 7.33 | 27.50 | 12.8 |
| 6 | 7.15 | 29.92 | 10.0 | 6.96 | 27.15 | 7.1 |
| 8 | — | — | | 7.09 | 29.37 | 9.1 |

TABLE X

Perm Efficiency Comparison With Varying Concentrations of Glycerylmonothioglycolate

| | Dithiol Compound 30% by Wgt. | | | Dithiol Compound 0% | | |
|---|---|---|---|---|---|---|
| % GMTG | D (mm) | L (mm) | D.I.T. | D (mm) | L (mm) | D.I.T. |
| 2 | 9.15 | 28.20 | 40.8 | 13.18 | 31.65 | 103 |
| 5 | 7.85 | 27.83 | 20.8 | 10.47 | 28.02 | 61.1 |
| 10 | 7.04 | 24.03 | 8.3 | 8.38 | 25.97 | 28.9 |
| 15 | 7.63 | 26.98 | 17.4 | 7.95 | 25.30 | 22.3 |

TABLE XI

Perm Efficiency Comparison With Varying Concentrations of Cysteamine Hydrochloride

| | Dithiol Compound 30% by Wgt. | | | Dithiol Compound 0% | | |
|---|---|---|---|---|---|---|
| % Cysteamine | D (mm) | L (mm) | D.I.T. | D (mm) | L (mm) | D.I.T. |
| 1 | 7.88 | 26.23 | 21.2 | 11.62 | 29.80 | 78.8 |
| 2 | 7.43 | 22.06 | 14.3 | 9.49 | 25.48 | 46.0 |
| 4 | 7.30 | 21.39 | 12.3 | 7.88 | 25.23 | 21.2 |
| 6 | 7.37 | 23.83 | 13.4 | 7.11 | 23.60 | 9.4 |

As is evident from a review of Tables VIII, IX, X, and XI, the incorporation of small amounts of a reduction booster produces a synergistic effect with the dithiol compound of Formula I. Furthermore, the hair fibers permed with this combination exhibited greater condition, shine, luster and tensile strength than hair permed with the dithiol compound of Formula I which did not incorporate the booster.

EXAMPLE 6

In order to further demonstrate the efficacy of incorporating a reduction booster in a permanent waving lotion incorporating a dithiol compound of Formula I, additional tests were conducted to determine the tensile strength of the resulting hair fibers. In order to best demonstrate the increased tensile strength resulting from the use of the present invention in combination with a small amount of a reduction booster, the 20% index of the resulting hair fibers were measured.

As is well known, the 20% index is a measure of the hair fiber damage in the yield region and is defined as the force ratio of treated to untreated hair fiber at 20% elongation. This method is commonly used to evaluate the damage being imparted to hair fibers.

In the tests conducted using the present invention, tinted hair was permed with a perming lotion incorporating a dithiol compound defined by Formula I which also incorporated a booster selected from the group consisting of ammonium thioglycolate, ammonium thiolactate, glycerylmonothioglycolate and cysteamine. The results attained are provided in Table XII along with the D.I.T. measurements. For purposes of comparison, the identical information is provided for hair permanently waved with a lotion incorporating a typical quantity of the booster composition without the dithiol compound of this invention.

TABLE XII

20% Index Data on Hair Fibers Treated with Dithiol Compounds (Formula I) Containing "Boosters" such as AMTG, AMTL, GMTG, and Cysteamine

| Reducing Solution | 20% Index | D (mm) | L (mm) | D.I.T. |
| --- | --- | --- | --- | --- |
| 2% AMTL + 30% POEDMA (M.W 548), pH 9.0 | 0.815 | 6.98 | 25.83 | 7.4 |
| 2% AMTG + 30% POEDMA (M.W 548), pH 9.0 | 0.790 | 6.92 | 22.04 | 6.5 |
| 2% Cysteamine + 30% POEDMA (M.W 548), pH 9.0 | 0.833 | 7.30 | 21.39 | 12.3 |
| 10% GMTG + 30% POEDMA (M.W 548), pH 9.0 | 0.849 | 7.04 | 24.03 | 8.3 |
| 6% AMTL, pH 9.0 | 0.704 | 6.96 | 27.15 | 7.1 |
| 6% AMTG, pH 9.0 | 0.613 | 7.13 | 26.13 | 9.7 |
| 6% Cysteamine, pH 9.0 | 0.734 | 7.11 | 23.60 | 9.4 |
| 30% GMTG, pH 9.0 | 0.792 | 7.20 | 24.30 | 10.8 |

POEDMA = Polyoxyethyleneglycol dimercaptoacetate

In order to effectively measure the tensile strength of the hair, an Instron Apparatus Model 1120 was used with each of the sample detailed above, with the resistant forces for each of the hair fibers being determined at 20% elongation under aqueous immersion conditions. The overall results attained from these elongation tests are provided in Table XII. The values provided represent the initial reading (prior to treatment) minus the final reading (after treatment) divided by the initial reading. As a result, the values closest to 1.000 indicate stronger relative tensile properties.

As is evident from a review of Table XII, the use of the dithiol compound defined by Formula I of the present invention along with a small amount of a reduction booster substantially improves the 20% index of the resulting hair fibers. This effect is particularly evident when the results obtained are compared to conventional permanent waving lotions which do not incorporate any dithiol compound.

EXAMPLE 7

In Table XIII, the waving efficiency of dithiol compounds of Formula I on tinted hair are provided for varying molecular weights. In each instance, R, R'=COCH$_2$SH with "n" ranging between 2 and 9. Each permanent wave formulation comprises a concentration of 1.0N, a pH of 9 and was processed at 37° C. for 15 minutes.

TABLE XIII

Perming Efficiency of Different Dithiol Compounds of Formula I on Resistant Hair

| M.W | D (mm) | L (mm) | D.I.T. |
| --- | --- | --- | --- |
| 348 | 6.98 | 26.33 | 7.38 |
| 548 | 9.03 | 27.33 | 38.9 |
| 748 | 19.90 | 30.50 | — |
| 776 | 11.20 | 32.25 | — |

As is evident from the results detailed in Table XIII, it is apparent that resistant hair can be effectively permanently waved at 37° C. with a dithiol compound of Formula I having a molecular weight of 348 or less, without requiring the use of a "booster". However, where the dithiol compound comprises a molecular weight greater than 348, a "booster" is required for obtaining acceptable permanent wave settings at 37° C.

It will thus be seen that the objects set forth above, among those made apparent from the preceding description, are efficiently attained and, since certain changes may be made in the compositions detailed herein, as well as in carrying out the above process, without departing from the scope of the invention, it is intended that all matter contained in the above description shall be interpreted as illustrative and not in a limiting sense.

It is to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients whenever the sense permits.

Having described our invention, what we claim as new and desire to secure by Letters Patent is:

1. A hair reducing or permanent waving lotion for use in the permanent waving of hair, said lotion comprising A. between about 5% and 40% by weight of the total composition of a reducing agent comprising at least one polyoxyethyleneglycol dimercaptoalkyl-ester having the formula R—OCH$_2$CH$_2$(—OCH$_2$CH$_2$)$_n$—OCH$_2$CH$_2$CO—R' where n is 2 to 33, and

R, R' = COCH$_2$SH
= COCH$_2$CH$_2$SH
= COCH$_2$CH$_2$CH$_2$SH
= COCHSHCH$_3$
= COCH(NH$_2$)CH$_2$SH
= COCH$_2$(NH$_2$)CH$_2$CH$_2$SH
= COCH$_2$CH(NH$_2$)CH$_2$SH;

B. between about 2% and 6% by weight of an ionic or non-ionic detergent;
C. between about 1% and 2% by weight of ammonium chloride;
D. between about 2% and 6% by weight of a penetrating agent; and
E. the balance comprising one or more agents selected from the group consisting of protein hydrolyzates, chelating agents, wetting agents, fragrances, conditioning agents and water.

2. The permanent waving lotion defined in claim 1, wherein said lotion is further defined as comprising an alkaline agent selected from the group consisting of ammonium, monoethanolamine, diethanolamine, triethanolamine, ammonium carbonate, and bicarbonate in sufficient amount to adjust the pH of the lotion to range between about 6.5 and 10.

3. The permanent waving lotion defined in claim 2, wherein the penetrating agent is further defined as comprising one selected from the group consisting of urea, pyrrolidone and phytantriol.

4. The permanent waving lotion defined in claim 3, wherein the reducing agent is further defined as comprising between about 20% and 30% by weight of the lotion composition.

5. A process for providing enhanced permanent waving of hair with substantially less malodor being produced, said process comprising the steps of
A. forming a permanent waving lotion comprising
a. between about 5% and 40% by weight of a polyoxyethyleneglycol dimercaptoalkylester compound having the formula

[R—OCH$_2$CH$_2$(—OCH$_2$CH$_2$O—)$_n$—CH$_2$CH$_2$CO—R']

R—OCH$_2$CH$_2$(—OCH$_2$CH$_2$)$_n$—OCH$_2$CH$_2$CO—R' where n is 2 to 33, and

R, R' = COCH$_2$SH
= COCH$_2$CH$_2$SH
= COCH$_2$CH$_2$CH$_2$SH
= COCHSHCH$_3$
= COCH(NH$_2$)CH$_2$SH
= COCH$_2$(NH$_2$)CH$_2$CH$_2$SH
= COCH$_2$CH(NH$_2$)CH$_2$SH, b. between about 2% and 6% by weight of an ionic or non-ionic detergent,
c. between about 1% and 2% by weight of ammonium chloride,
d. between about 2% and 6% by weight of a penetrating agent and
e. water forming the balance;
B. moistening hair to be permanently waved;
C. rolling the moistened hair fibers onto curlers for securement thereto;
D. applying the permanent waving lotion to the rolled hair fibers;
E. allowing the permanent waving lotion to remain on the hair for between about 10 and 60 minutes;
F. rinsing the hair with water and blotting to remove excess moisture; and
G. neutralizing or oxidizing the hair by employing a solution comprising one or more agents selected from the group consisting of acidic hydrogen peroxide, alkaline bromate, and sodium chloride.

6. The process defined in claim 5, wherein said permanent waving lotion is further defined as comprising an alkaline agent selected from the group consisting of ammonium, monoethanolamine, diethanolamine, triethanolamine, ammonium carbonate, and bicarbonate in sufficient amount to adjust the pH of the permanent waving lotion to range between about 6.5 and 10.

7. The process defined in claim 5, comprising the additional step of
H. heating the hair during the processing of the permanent waving lotion.

8. The process defined in claim 7, wherein said hair is further defined as being heated to a temperature ranging between about 35° C. and 75° C.

9. The process defined in claim 5; wherein the permanent waving lotion is further defined as being prepared by intermixing all of the components therefor except the "polyoxyethyleneglycol dimercaptoalkylester" reducing agent and intermixing the polyoxyethyleneglycol dimercaptoalkylester reducing agent with the previously prepared additives immediately prior to applying the permanent waving lotion to the head of hair to be permanently waved.

10. The process defined in claim 5, wherein said permanent waving lotion is further defined as comprising
c. at least one reducing booster selected from the group consisting of ammonium thioglycolate, ammonium thiolactate, glycerol monothioglycolate, glycerol monothiolactate, cysteamine, and cysteine.

11. The process defined in claim 10, wherein said reducing booster is further defined as comprising between about 1% and 6% by weight of the permanent waving lotion.

12. A hair reducing or permanent waving lotion for use in the permanent waving of hair, said lotion comprising
A. between about 5% and 40% by weight of the total composition of a reducing agent comprising at least one polyoxyethyleneglycol dimercaptoalkyl-ester having the formula R—OCH$_2$CH$_2$(—OCH$_2$CH$_2$)$_n$—OCH$_2$CH$_2$CO—R' where n is 2 to 33, and

R, R' = COCH$_2$SH
 = COCH$_2$CH$_2$SH
 = COCH$_2$CH$_2$CH$_2$SH
 = COCHSHCH$_3$
 = COCH(NH$_2$)CH$_2$SH
 = COCH$_2$(NH$_2$)CH$_2$CH$_2$SH
 = COCH$_2$CH(NH$_2$)CH$_2$SH; and B. between about 2% and 6% by weight of an ionic or non-ionic detergent;

C. between about 1% and 2% by weight of ammonium chloride;

D. between about 2% and 6% by weight of a penetrating agent; and

E. an alkaline agent selected from the group consisting of ammonium, monoethanolamine, diethanolamine, triethanolamine, ammonium carbonate, and bicarbonate in sufficient amount to adjust the pH of the lotion to range between about 6.5 and 10; and F. the balance comprising one or more agents selected from the group consisting of penetrating agents, protein hydrolyzates, chelating agents wetting agents, fragrances, conditioning agents, and water.

* * * * *

UNITED STATES PATENT AND TRADEMARK OFFICE
CERTIFICATE OF CORRECTION

PATENT NO. :  5,350,572
DATED      :  September 27, 1994
INVENTOR(S):  Savaides et al It is certified that error appears in the above—identified patent and that said Letters Patent is hereby corrected as shown below:

On the title page, where the (*) Notice: is printed, the Notice reads "The portion of this patent subsequent to Sep. 7, 2000 has been disclaimed."

The Notice should read

-- The portion of the term of this patent subsequent to Sep. 7, 2010 has been disclaimed. --

Signed and Sealed this

Third Day of January, 1995

*Attest:*

BRUCE LEHMAN

*Attesting Officer*      *Commissioner of Patents and Trademarks*